US008921589B2

(12) United States Patent
Kawata et al.

(10) Patent No.: US 8,921,589 B2
(45) Date of Patent: Dec. 30, 2014

(54) ELECTROLYTE FORMULATIONS

(75) Inventors: Kentaro Kawata, Kanagawa Pref. (JP);
Nikolai Mykola Ignatyev, Duisburg (DE); Michael Schulte, Bischofsheim (DE); Hiroki Yoshizaki, Tokyo (JP)

(73) Assignee: Merck Patent GmbH, Darmstadt (DE)

( * ) Notice: Subject to any disclaimer, the term of this patent is extended or adjusted under 35 U.S.C. 154(b) by 4 days.

(21) Appl. No.: 13/876,414

(22) PCT Filed: Sep. 1, 2011

(86) PCT No.: PCT/EP2011/004419
§ 371 (c)(1),
(2), (4) Date: Mar. 27, 2013

(87) PCT Pub. No.: WO2012/041437
PCT Pub. Date: Apr. 5, 2012

(65) Prior Publication Data
US 2013/0180591 A1    Jul. 18, 2013

(30) Foreign Application Priority Data
Sep. 30, 2010    (EP) .................................... 10011965

(51) Int. Cl.
*C07F 5/02*    (2006.01)
*H01G 9/022*    (2006.01)
*C07F 5/00*    (2006.01)
*H01G 9/035*    (2006.01)
*H01G 9/20*    (2006.01)
*H01G 11/62*    (2013.01)

(52) U.S. Cl.
CPC ............... *H01G 9/022* (2013.01); *C07F 5/006* (2013.01); *H01G 9/035* (2013.01); *H01G 9/038* (2013.01); *H01G 9/2013* (2013.01); *H01G 11/62* (2013.01); *Y02E 10/542* (2013.01); *Y02E 60/13* (2013.01)
USPC ........................................................ 558/384

(58) Field of Classification Search
CPC ....................................................... C07F 5/006
USPC ............................................................ 558/384
See application file for complete search history.

(56) References Cited

U.S. PATENT DOCUMENTS

| 7,645,434 | B2 * | 1/2010 | Welz-Biermann et al. ... 423/377 |
| 7,872,191 | B2 | 1/2011 | Usui et al. |
| 8,114,318 | B2 | 2/2012 | Kuang et al. |
| 2006/0174932 | A1 | 8/2006 | Usui et al. |
| 2006/0222584 | A1 * | 10/2006 | Welz-Biermann et al. ... 423/377 |
| 2009/0253031 | A1 | 10/2009 | Usui et al. |
| 2009/0293953 | A1 | 12/2009 | Usui et al. |
| 2010/0229950 | A1 | 9/2010 | Kuang et al. |
| 2011/0012048 | A1 | 1/2011 | Zhang et al. |

FOREIGN PATENT DOCUMENTS

| EP | 1 653 549 | 5/2006 |
| JP | 2004 175666 | 6/2004 |
| WO | WO-2004 072089 | 8/2004 |
| WO | WO-2007 093961 | 8/2007 |
| WO | WO-2009 083901 | 7/2009 |

OTHER PUBLICATIONS

International Search Report for PCT/EP2011/004419; Date of the actual completion of the international search: Mar. 28, 2012, Date of mailing of the international search report: Apr. 3, 2012.
Tokuyama Corp., "Onium Salt," Patent Abstracts of Japan, Publication Date: Jun. 24, 2004; English Abstract of JP-2004 175666.
Gorlov, M. et al., "Ionic liquid electrolytes for dye-sensitized solar cells," Dalton Trans, 2008, pp. 2655-2666.

* cited by examiner

*Primary Examiner* — Joseph Kosack
(74) *Attorney, Agent, or Firm* — Millen, White, Zelano & Branigan, P.C.

(57) ABSTRACT

The present invention relates to electrolyte formulations comprising at least one imidazolium fluorotricyanoborate or pyrrolidinium fluorotricyanoborate and their use in an electrochemical and/or optoelectronic device such as a photovoltaic cell, a light emitting device, an electrochromic or photoelectrochromic device, an electrochemical sensor and/or biosensor, preferably their use in a dye or quantum dot sensitized solar cell.

27 Claims, No Drawings

ELECTROLYTE FORMULATIONS

The present invention relates to electrolyte formulations comprising at least one imidazolium fluorotricyanoborate or pyrrolidinium fluorotricyanoborate and their use in an electrochemical and/or optoelectronic device such as a photovoltaic cell, a light emitting device, an electrochromic or photoelectrochromic device, an electrochemical sensor and/or biosensor, preferably their use in a dye or quantum dot sensitized solar cell.

Electrolyte formulations form a crucial part of electrochemical and/or optoelectronic devices and the performance of the device largely depends on the physical and chemical properties of the various components of these electrolytes.

The term electrolytes is used herein in the sense of electrolyte formulation as defined below and will be used equally to electrolyte formulation within the disclosure.

Factors which are still impeding the technical application of many electrochemical and/or optoelectronic devices and in particular of dye or quantum dot sensitized solar cells, are reliability problems caused by the volatility of organic solvents based electrolytes. It is very difficult to maintain a tight sealing of the electrolyte in e.g. a DSC panel, which has to withstand the temperature differences of daily day-night cycles and the concomitant thermal expansion of the electrolyte. The abbreviation DSC means dye sensitized solar cell. This problem can be solved in principle by the use of ionic liquid-based electrolytes. For review "Ionic liquid electrolytes for dye-sensitized solar cells" see: M. Gorlov and L. Kloo, *Dalton Trans.*, 2008, p. 2655-2666.

Ionic liquids or liquid salts are typically ionic species which consist of an organic cation and a generally inorganic anion usually having melting points below 373 K. Various binary ionic liquid electrolytes have recently been applied to dye-sensitized solar cells. WO 2007/093961 and WO 2009/083901 describe so far the best power conversion efficiencies in ionic liquid-based electrolytes for DSC containing a significant quantity of organic salts with tetracyanoborate (TCB) anions.

However, there continues to be a demand for new and improved electrolytes based on ionic liquids with improved DSC efficiency especially at a temperature below room temperature and well above the temperature at which liquid freezing and precipitation may take place (i.e. in the range of 0° C. to 20° C.).

The object of the invention is therefore to provide electrolyte formulations for electrochemical and/or optoelectronic devices with increased power conversion efficiency such as a photovoltaic cell, a light emitting device, an electrochromic or photo-electrochromic device, an electrochemical sensor and/or biosensor, especially for dye or quantum dot sensitized solar cells, especially preferably for dye sensitized solar cells over a broad temperature range, particularly additionally at low temperature. Low temperature is defined as the temperature range between 0° C. and 20° C.

Surprisingly it was found that electrolyte formulations comprising fluorotricyanoborate anions fulfill such demands.

It is believed that formulations comprising fluorotricyanoborate anions reduce the Nernst diffusion resistance of redox-couple species (e.g. $I^-$ and $I_3^-$) and charge transfer resistance at the counter electrode at low temperatures as defined above.

The present invention therefore relates firstly to an electrolyte formulation comprising at least one compound of formula (I)

$$Kt^+[BF(CN)_3]^- \quad (I)$$

in which $Kt^+$ is an organic cation selected from the group of

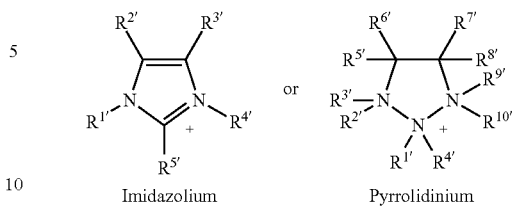

Imidazolium      Pyrrolidinium where the substituents
$R^{1'}$ to $R^{10'}$ each, independently of one another, denote
H with the assumption that $R^{1'}$ and $R^{4'}$ are not simultaneously H and are not perfluorinated at the same time,
straight-chain or branched alkyl having 1 to 20 C atoms, which optionally may be fluorinated or perfluorinated,
straight-chain or branched alkenyl having 2 to 20 C atoms and one or more double bonds, which optionally may be fluorinated or perfluorinated,
straight-chain or branched alkynyl having 2 to 20 C atoms and one or more triple bonds which optionally may be fluorinated or perfluorinated or
straight-chain or branched alkoxyalkyl having 2 to 8 C atoms.

Compounds of formula (I) with imidazolium cations are known from WO 2004/072089. However, WO 2004/072089 does not describe an electrolyte formulation comprising compounds of formula (I) as described above and it does not disclose the specific utility of these compounds as components of an electrolyte formulation for the given electrochemical and/or electrooptical devices, especially for DSC.

Similar organic salts are additionally described in JP2004-175666 which means onium salts with anions of formula $[(CN)_aX_{4-a}B]^-$ in which X is a halogen atom and a is an integer of 1 to 3. Trifluorocyanoborate is disclosed therein as preferred anion. In addition, this document merely discloses electrolyte formulations containing 1-ethyl-3-methylimidazolium trifluorocyanoborate, tetraethylammonium trifluorocyanoborate or trimethyl-propylammonium trifluorocyanoborate. There is no hint that compounds of formula (I) as described above would show such outstanding properties as shown below.

The present invention is therefore a selection invention out of the knowledge of the prior art.

The electrolyte formulations may include or comprise, essentially consist of or consist of the said necessary or optional constituents.

A straight-chain or branched alkyl having 1-20 C atoms denotes an alkyl group having 1, 2, 3, 4, 5, 6, 7, 8, 9, 10, 11, 12, 13, 14, 15, 16, 17, 18, 19 or 20 C atoms, for example methyl, ethyl, isopropyl, n-propyl, isobutyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or eicosyl, which optionally may be fluorinated or perfluorinated. The term "perfluorinated" means that all H atoms are substituted by F atoms in the given alkyl group. The term "fluorinated" means that at least one H atom of the given alkyl group is substituted by an F atom.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hex-enyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenyl, isopentenyl or hexenyl, which may be optionally fluorinated or perfluorinated.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propyn-yl, 2- or 3-butynyl, 4-pentynyl, 3-pentynyl or hexynyl, which may be optionally fluorinated or perfluorinated.

A straight-chain or branched alkoxyalkyl having 2 to 12 C atoms is, for example, methoxymethyl, 1-methoxyethyl, 1-methoxypropyl, 1-methoxy-2-methyl-ethyl, 2-methoxypropyl, 2-methoxy-2-methyl-propyl, 1-methoxybutyl, 1-methoxy-2,2-dimethyl-ethyl, 1-methoxy-pentyl, 1-methoxyhexyl, 1-methoxy-heptyl, ethoxymethyl, 1-ethoxyethyl, 1-ethoxypropyl, 1-ethoxy-2-methyl-ethyl, 1-ethoxybutyl, 1-ethoxy-2,2-dimethyl-ethyl, 1-ethoxypentyl, 1-ethoxyhexyl, 1-ethoxyheptyl, propoxymethyl, 1-propoxyethyl, 1-propoxypropyl, 1-propoxy-2-methyl-ethyl, 1-propoxybutyl, 1-propoxy-2,2-dimethyl-ethyl, 1-propoxypentyl, butoxymethyl, 1-butoxyethyl, 1-butoxypropyl or 1-butoxybutyl. Particularly preferred is methoxymethyl, 1-methoxyethyl, 2-methoxy-propyl, 1-methoxypropyl, 2-methoxy-2-methyl-propyl or 1-methoxybutyl.

The substituents $R^{1'}$ and $R^{4'}$ are each, independently of one another, preferably straight-chain or branched alkyl having 1 to 20 C atoms, which optionally may be fluorinated or perfluorinated or straight-chain or branched alkoxyalkyl having 2 to 8 C atoms with the assumption that $R^{1'}$ and $R^{4'}$ are not perfluorinated at the same time, particularly preferably methyl, ethyl, isopropyl, propyl, butyl, sec-butyl, tert-butyl, n-pentyl or n-hexyl. They are very particularly preferably methyl, ethyl, n-butyl or n-hexyl. In pyrrolidinium or imidazolium, the two substituents $R^{1'}$ and $R^{4'}$ are preferably different.

In accordance with the invention, suitable substituents $R^{2'}$, $R^{3'}$ and $R^{5'}$ to $R^{10'}$ of compounds of the formula (I), besides H for, are preferably: $C_1$- to $C_{20}$-alkyl groups, in particular $C_1$- to $C_6$-alkyl groups.

The substituents $R^{2'}$, $R^{3'}$, $R^{5'}$ to $R^{10'}$ are in each case, independently of one another, in particular H, methyl, ethyl, isopropyl, propyl, butyl, sec-butyl or tert-butyl. $R^{5'}$ of the imidazolium ring is particularly preferably H, methyl, ethyl, isopropyl, propyl or n-butyl, particularly preferably H or methyl. $R^{2'}$ and $R^{3'}$ of the imidazolium ring are preferably H. The substituents $R^{2'}$, $R^{3'}$, $R^{5'}$ to $R^{10'}$ of the pyrrolidinium ring are preferably H.

Preferred 1,1-dialkylpyrrolidinium cations are, for example, 1,1-dimethyl-pyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1,1-dinonylpyrrolidinium, 1-nonyl-1-decylpyrrolidinium or 1,1-didecylpyrrolidinium. Very particular preference is given to 1-butyl-1-methylpyrrolidinium or 1-propyl-1-methylpyrrolidinium.

Preferred 1-alkyl-1-alkoxyalkylpyrrolidinium cations are, for example, 1-(2-methoxyethyl)-1-methylpyrrolidinium, 1-(2-methoxyethyl)-1-ethylpyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-methylpyrrolidinium. Very particular preference is given to 1-(2-methoxyethyl)-1-methylpyrrolidinium.

Preferred 1,3-dialkylimidazolium cations are, for example, 1-ethyl-3-methylimidazolium, 1-methyl-3-propylimidazolium, 1-methyl-2,3-dimethylimidazolium, 1-ethyl-2,3-dimethylimidazolium, 1-propyl-2,3-dimethylimidazolium, 1-butyl-2,3-dimethylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methylimidazolium, 1-butyl-3-methylimidazolium or 1-methyl-3-propylimidazolium.

Preferred 1-alkoxyalkyl-3-alkylimidazolium cations are, for example 1-(2-methoxyethyl)-3-methylimidazolium, 1-(2-methoxyethyl)-3-ethylimidazolium, 1-(2-methoxyethyl)-3-propylimidazolium, 1-(2-methoxyethyl)-3-butylimidazolium, 1-(2-ethoxyethyl)-3-methylimidazolium, 1-ethoxymethyl-3-methylimidazolium.

Preferred 1-alkenyl-3-alkylimidazolium cations are, for example 1-allyl-3-methyl-imidazolium or 1-allyl-2,3-dimethylimidazolium.

In chemistry, an electrolyte is any substance containing free ions that make the substance electrically conductive. The most typical electrolyte is an ionic solution, but molten electrolytes and solid electrolytes are also possible.

An electrolyte formulation according to the invention is therefore an electrically conductive medium, basically due to the presence of at least one substance that is present in a dissolved and or in molten state i.e. supporting an electric conductivity via motion of ionic species.

The term electrolyte may be used for the term electrolyte formulation as well comprising all ingredients as disclosed for the electrolyte formulation.

Particularly preferably, the electrolyte formulation according to the invention comprise at least one compound of formula (I) with the given formula for imidazolium as described or preferably described above.

The present invention relates further to an electrolyte formulation comprising at least one compound of formula (I) as described above in which Kt⁺ of the compound of formula (I) is

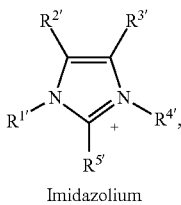

Imidazolium where the substituents $R^{2'}$ and $R^{3'}$ are H, $R^{5'}$ is H or straight-chain or branched alkyl having 1 to 4 C atoms and $R^{1'}$ and $R^{4'}$ are each independently of one another straight chain or branched alkyl having 1-20 C atoms or straight-chain or branched alkenyl having 3 C atoms.

The present invention relates also to an electrolyte formulation comprising at least one compound of formula (I) in which Kt⁺ of the compound of formula (I) is

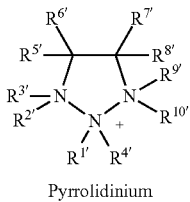

Pyrrolidinium where the substituents $R^{2'}$, $R^{3'}$, $R^{5'}$ to $R^{10'}$ are H and $R^{1'}$ and $R^{4'}$ are each independently of one another straight chain or branched alkyl having 1-20 C atoms.

Particularly preferably, the electrolyte formulation according to the invention comprise at least one compound of formula (I) with the given formula for imidazolium and the definitions of the substituents $R^{1'}$, to $R^{5'}$ or particularly preferred meanings of dialkylimidazolium or 1-alkoxyalkyl-3-alkylimidazolium as described above.

Typical molar concentrations of the fluorotricyanoborate anion in the electrolyte formulations range from 0.1 to 5.5 M, preferably from 0.8 to 3.5 M. This molar concentration in the electrolyte may be achieved with one or more compounds of formula (I) or with mixtures comprising at least one compound of formula (I) and at least one inorganic salt with the fluorotricyanoborate anion.

Inorganic salts with fluorotricyanoborate anions are for example lithium fluorotricyanoborate, sodium fluorotricyanoborate, potassium fluorotricyanoborate, silver fluorotricyanoborate, magnesium di(fluorotricyanoborate), calcium di(fluorotricyanoborate) or zinc di(fluorotricyanoborate).

Preferably, the molar concentration is achieved with at least one compound of formula (I) as described or preferably described above. For the purpose of the present invention, the molar concentration refer to the concentration at 25° C.

Other components of the electrolyte formulation are one or several further salts, solvents, iodine and others, as indicated further below.

If the electrolyte formulation is a binary system, it comprises two salts, one further salt and a compound of formula (I) as described above. If the electrolyte formulation is a ternary system, it comprises two further salts and a compound of formula (I) as described above. The binary system comprises 90-20 weight %, preferably 80-55 weight %, more preferably 70-60 weight % of the further salt and 10-80 weight %, preferably 20-45 weight or more preferably 30-40 weight % of the compound of formula (I) as described above. The percentages in this paragraph are expressed with respect to the total of salts (=100 weight %) present in the electrolyte formulation according to the invention. Amounts of further, generally optional components (additives) indicated below, such as N-containing compounds having unshared electron pairs, iodine, solvents, polymers, and nanoparticles, for example, are not considered therein. The same percentages apply to ternary or quaternary systems which means the total of the further salts has to be used in the given ranges, e.g. two further ionic liquids are comprised in e.g. 90-20 weight. % in the electrolyte formulation according to the invention.

According to another embodiment of the present invention, the electrolyte formulation comprises at least one further salt with organic cations comprising a quaternary nitrogen and an anion selected from a halide ion, such as F⁻, Cl⁻, I⁻, a polyhalide ion, a fluoroalkanesulfonate, a fluoroalkanecarboxylate, a tri(fluoroalkylsulfonyl)methide, a bis(fluoroalkylsulfonyl)imide, a nitrate, a hexafluorophosphate, a tris-, bis- and mono-(fluoroalkyl)fluorophosphate, a tetrafluoroborate, a dicyanamide, a tricyanomethide, a tetracyanoborate, a thiocyanate, an alkylsulfonate or an alkylsulfate, with fluoroalkane having 1 to 20 C atoms, preferably perfluorinated, fluoroalkyl having 1 to 20 C atoms and alkyl having 1 to 20 C atoms. Fluoroalkane or fluoroalkyl is preferably perfluorinated.

Preferably, the further salts are selected from salts comprising anions such as iodide, thiocyanate or tetracyanoborate, particularly preferred further salts are iodides.

The cation of the at least one further salt or of a preferred further salt may be selected amongst organic compounds comprising a quaternary nitrogen atom, preferably cyclic organic cations such as pyridinium, imidazolium, triazolium, pyrrolidinium or morpholinium.

However, to limit the amount of different cations in the electrolyte formulations, especially for DSC, the organic cations may be selected from the definitions for the cations of the compounds of formula (I). Therefore, according to another preferred embodiment of the present invention, the electrolyte formulation comprises at least one compound of formula (I) as described above and at least one further iodide in which the organic cations are independently selected from the group of,

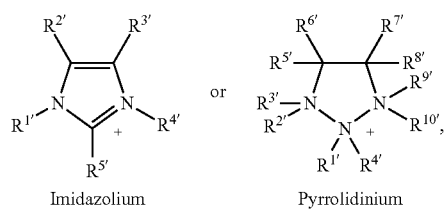

Imidazolium      Pyrrolidinium in which the substituents $R^{1'}$ to $R^{10'}$ have a meaning as described or preferably described above.

Particularly preferred examples of the at least one further salt are 1-ethyl-3-methylimidazolium iodide, 1-propyl-3-methylimidazolium iodide, 1-butyl-3-methyl-imidazolium iodide, 1-hexyl-3-methylimidazolium iodide, 1,3-dimethylimidazolium iodide, 1-allyl-3-methylimidazolium iodide, N-butyl-N-methyl-pyrrolidinium iodide or N,N-dimethyl-pyrrolidinium iodide.

In another embodiment of the invention, guanidinium thiocyanate may be added to the electrolyte formulation according to the invention.

The electrolyte formulation of the invention preferably comprises iodine ($I_2$). Preferably, it comprises from 0.0005 to 7 mol/dm$^3$, more preferably 0.01 to mol/dm$^3$ and most preferably from 0.05 to 1 mol/dm$^3$ of $I_2$.

In a preferred embodiment, the electrolyte formulation of the present invention further comprises at least one compound containing a nitrogen atom having non-shared electron pairs. Examples of such compounds are found in EP 0 986 079 A2, starting on page 2, lines 40-55, and again from page 3, lines 14 extending to page 7, line 54, which are expressly incorporated herein by reference. Preferred examples of compounds having non-shared electron pairs include imidazole and its derivatives, particularly benzimidazole and its derivatives.

The electrolyte formulation of the present invention comprises less than 50 vol. % of an organic solvent. Preferably, the electrolyte formulation comprises less than 40%, more preferably less than 30%, still more preferably less than 20% and even less than 10%. Most preferably, the electrolyte formulation comprises less than 5% of an organic solvent. For example, it is substantially free of an organic solvent. Percentages are indicated on the basis of weight %.

Organic solvents, if present in such amounts as indicated above, may be selected from those disclosed in the literature. Preferably, the solvent, if present, has a boiling point higher than 160 degrees centigrade, more preferably higher than 190 degrees such as propylene carbonate, ethylene carbonate, butylene carbonate, gamma-butyrolactone, gamma-valerolactone, glutaronitrile, adiponitrile, N-methyloxazolidinone, N-methylpyrrolidinone, N,N'-dimethylimidazolidinone, N,N-dimethylacetamide, cyclic ureas preferably 1,3-dimethyl-2-imidazolidinone or 1,3-dimethyl-3,4,5,6-tetrahydro-2(1H)-pyrimidinone, glymes preferably tetraglyme, sulfolane, sulfones which are preferably asymmetrically substituted such as 2-ethanesulfonyl-propane, 1-ethanesulfonyl-2-methyl-propane or 2-(propane-2-sulfonyl)-butane, 3-methylsulfolane, dimethylsulfoxide, trimethylphosphate and methoxy-substituted nitriles. Other useful solvents are acetonitrile, benzonitrile and or valeronitrile.

If a solvent is present in the electrolyte formulation, there may further be comprised a polymer as gelling agent, wherein the polymer is polyvinylidenefluoride, polyvinylidene-hexafluoropropylene, polyvinylidene-hexafluoropropylene-chlorotrifluoroethylene copolymers, nafion, polyethylene oxide, polymethylmethacrylate, polyacrylonitrile, polypropylene, polystyrene, polybutadiene, polyethyleneglycol, polyvinylpyrrolidone, polyaniline, polypyrrole, polythiophene. The purpose of adding these polymers to electrolyte formulations is to make liquid electrolytes into quasi-solid or solid electrolytes, thus improving solvent retention, especially during aging.

The electrolyte formulation of the invention may further comprise metal oxide nanoparticles like $SiO_2$, $TiO_2$, $Al_2O_3$, MgO or ZnO, for example, which are also capable of increasing solidity and thus solvent retention.

The electrolyte formulation of the invention has many applications. For example, it may be used in an optoelectronic and/or electrochemical device such as a photovoltaic cell, a light emitting device, an electrochromic or photo-electrochromic device, an electrochemical sensor and/or biosensor. Also the use in electrochemical batteries is possible, for example in a lithium ion battery or a double layer capacitor.

The present invention therefore relates further to the use of the electrolyte formulation as described in detail above in an electrochemical and/or optoelectronic device which is a photovoltaic cell, a light emitting device, an electrochromic or photo-electrochromic device, an electrochemical sensor and/or biosensor. Preferably, the electrolyte formulation may be used in dye sensitized solar cells.

The present invention therefore relates furthermore to an electrochemical and/or optoelectronic device which is a photovoltaic cell, a light emitting device, an electrochromic or photo-electrochromic device, an electrochemical sensor and/or biosensor comprising an electrolyte formulation comprising at least one compound of formula (I)

$$Kt^+[BF(CN)_3]^- \qquad (I)$$

in which $Kt^+$ is an organic cation selected from the group of,

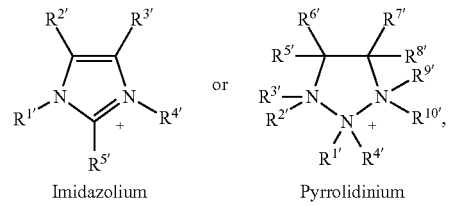

Imidazolium      Pyrrolidinium where the substituents
$R^{1'}$ to $R^{10'}$ each, independently of one another, denote
H with the assumption that $R^{1'}$ and $R^{4'}$ are not simultaneously H and are not perfluorinated at the same time,
straight-chain or branched alkyl having 1-20 C atoms, which optionally may be fluorinated or perfluorinated,
straight-chain or branched alkenyl having 2-20 C atoms and one or more double bonds, which optionally may be fluorinated or perfluorinated,
straight-chain or branched alkynyl having 2-20 C atoms and one or more triple bonds which optionally may be fluorinated or perfluorinated or
straight-chain or branched alkoxyalkyl having 2 to 8 C atoms.

According to a preferred embodiment, the device of the present invention is a dye or quantum dot sensitized solar cell, particularly preferably a dye sensitized solar cell.

Quantum dot sensitized solar cells are disclosed in U.S. Pat. No. 6,861,722, for example. In dye-sensitized solar cells, a dye is used to absorb the sunlight to convert into the electrical energy. Examples of dyes are disclosed in EP 0 986 079 A2, EP 1 180 774 A2 or EP 1 507 307 A1.

Preferred dyes are organic dyes such as MK-1, MK-2 or MK-3 (its structures are described in FIG. 1 of N. Koumura et al, J. Am. Chem. Soc. Vol 128, no. 44, 2006, 14256-14257), D102 (CAS no. 652145-28-3), D-149 (CAS no. 786643-20-7), D205 (CAS no. 936336-21-9), YD-2 as described in T. Bessho et al, Angew. Chem. Int. Ed. Vol 49, 37, 6646-6649, 2010, Y123 (CAS no. 1312465-92-1), bipyridin-Ruthenium dyes such as N3 (CAS no. 141460-19-7), N719 (CAS no. 207347-46-4), Z907 (CAS no. 502693-09-6), C101 (CAS no. 1048964-93-7), C106 (CAS no. 1152310-69-4), K19 (CAS no. 847665-45-6) or terpyridine-Ruthenium dyes such as N749 (CAS no. 359415-47-7).

Particularly preferred dyes are Z907 or Z907Na which are both an amphiphilic ruthenium sensitizer.

In a preferred embodiment, the dye is coadsorbed with a phosphinic acid. A preferred example of a phosphinic acid is bis(3,3-dimethyl-butyl)-phosphinic acid (DINHOP) as disclosed in M. Wang et al, Dalton Trans., 2009, 10015-10020.

The dye Z907Na means NaRu(2,2'-bipyridine-4-carboxylic acid-4'-carboxylate)(4,4'-dinonyl-2,2'-bipyridine)(NCS)$_2$.

For example, a dye-sensitized solar cell comprises a photo-electrode, a counter electrode and, between the photo-electrode and the counter electrode, an electrolyte formulation or a charge transporting material, and wherein a sensitizing dye is absorbed on the surface of the photo-electrode, on the side facing the counter electrode.

According to a preferred embodiment of the device according to the invention, it comprises a semiconductor, the electrolyte formulation as described above and a counter electrode.

According to a preferred embodiment of the invention, the semiconductor is based on material selected from the group of Si, TiO$_2$, SnO$_2$, Fe$_2$O$_3$, WO$_3$, ZnO, Nb$_2$O$_5$, CdS, ZnS, PbS, Bi$_2$S$_3$, CdSe, GaP, InP, GaAs, CdTe, CuInS$_2$, and/or CuInSe$_2$. Preferably, the semiconductor comprises a mesoporous surface, thus increasing the surface optionally covered by a dye and being in contact with the electrolyte. Preferably, the semiconductor is present on a glass support or plastic or metal foil. Preferably, the support is conductive.

The device of the present invention preferably comprises a counter electrode. For example, fluorine doped tin oxide or tin doped indium oxide on glass (FTO- or ITO-glass, respectively) coated with Pt, carbon of preferably conductive allotropes, polyaniline or poly(3,4-ethylenedioxythiophene) (PEDOT). Metal substrates such as stainless steel or titanium sheet may be possible substrates beside glass.

The device of the present invention may be manufactured as the corresponding device of the prior art by simply replacing the electrolyte by the electrolyte formulation of the present invention. For example, in the case of dye-sensitized solar cells, device assembly is disclosed in numerous patent literature, for example WO 91/16719 (examples 34 and 35), but also scientific literature, for example in Barbé, C. J., Arendse, F., Comte, P., Jirousek, M., Lenzmann, F., Shklover, V., Grätzel, M. J. Am. Ceram. Soc. 1997, 80, 3157; and Wang, P., Zakeeruddin, S. M., Comte, P., Charvet, R., Humphry-Baker, R., Grätzel, M. J. Phys. Chem. B 2003, 107, 14336.

Unlike electrochemical devices which require much more power density such as capacitors the DSC does not require high conductivity of the liquid electrolyte. For example in DSC, the electrode resistance of electrolyte at 10° C. is estimated by semiconductor electrode thickness divided by electrolyte conductivity, typically at 10 μm/10 mScm$^{-1}$=0.01 Ωcm$^2$.

Preferably, the sensitized semiconducting material serves as a photoanode. Preferably, the counter electrode is a cathode.

The present invention provides a method for preparing a photoelectric cell comprising the step of bringing the electrolyte formulation of the invention in contact with a surface of a semiconductor, said surface optionally being coated with a sensitizer. Preferably, the semiconductor is selected from the materials given above, and the sensitizer is preferably selected from quantum dots and/or a dye as disclosed above, particularly preferably selected from a dye.

Preferably, the electrolyte formulation may simply be poured on the semiconductor. Preferably, it is applied to the otherwise completed device already comprising a counter electrode by creating a vacuum in the internal lumen of the cell through a hole in the counter electrode and adding the electrolyte formulation as disclosed in the reference of Wang et al., J. Phys. Chem. B 2003, 107, 14336.

The present invention will now be illustrated, without limiting its scope, by way of the following examples:

EXAMPLE 1

Synthesis, Characterisation and Viscosity/Conductivity Measurements of 1-ethyl-3-methylimidzolium tetracyanoborate (emim TCB) and 1-ethyl-3-methylimidzolium fluorotricyanoborate)

Ethyl-3-methylimidzolium tetracyanoborate and 1-ethyl-3-methylimidazolium fluorotricyanoborate are synthesized according to WO 2004/072089, examples 9 and 12 and E. Bernhardt et al., Z. Anorg. Allg. Chem., 2003, 629, 677-685.

Table 1 gives specific parameters of the ionic liquids used:

TABLE 1 gives specific parameters of the ionic liquids used:

| Compound | T [° C.] | Density [g/cm$^3$] | Dynamic viscosity [mPa/s] | Specific conductivity [mS/cm] |
|---|---|---|---|---|
| emim TCB* | 20 | 1.04 | 22.2 | 13.0 |
|  | 40 | 1.03 | 11.2 | 23.2 |
|  | 60 | 1.01 | 6.75 | 35.9 |
|  | 80 | 1.00 | 4.53 | 50.5 |
| emim fluorotricyanoborate | 20 | 1.07 | 12.6 |  |
|  | 40 | 1.06 | 7.5 |  |
|  | 60 | 1.04 | 5.0 |  |
|  | 80 | 1.03 | 3.6 |  |

*not according to the invention

EXAMPLE 2

Formulations and Device

The following electrolyte formulations are synthesized to demonstrate the unexpected advantage of electrolyte formulations according to the invention relative to electrolyte formulations of the prior art containing emim TCB.

The electrolyte formulations are prepared through mixing of one or more of 1,3-dimethylimidazolium iodide (mmimI), 1-ethyl-3-methylimidazolium iodide (emimI) and 1-methyl-3-propylimidazolium iodide (pmimI), 1-allyl-3-methylimidazolium iodide (amim I), 1-hydroxymethyl-3-methylimidazolium iodide (mohmim I), 1,1-dimethylpyrrolidinium iodide (mmplI), trimethylsulfonium iodide (sm3 I), iodine, N-butylbenzimidazole (NBB) and guanidinium thiocyanate (guaSCN) and the corresponding ionic liquid as indicated such as emim TCB or emim fluorotricyanoborate in the molar ratio as listed below. It may be necessary to apply heat up to 120° C. to make the electrolyte formulation homogeneous.

Electrolyte 1 given in the molar ratio:
36 mmim I, 36 pmim I, 72 emim TCB
Electrolyte 2 given in the molar ratio:
36 mmim I, 36 emim I, 72 emim TCB
Electrolyte 3 given in the molar ratio:
36 mmim I, 36 amim I, 72 emim TCB
Electrolyte 4 given in the molar ratio:
72 emim I, 72 emim TCB
Electrolyte 5 given in the molar ratio:
36 mmim, 36 mohmim I, 72 emim TCB
Electrolyte 6 given in the molar ratio:
36 mmim I, 36 mmpl I, 72 emim TCB Electrolyte 7 given in the molar ratio:
36 mmim I, 36 sm3 I, 72 emim TCB
Electrolyte 8 given in the molar ratio:
36 mmim I, 8 pmim I, 12 amim I, 8 hmim I, 8 mmpl I, 72 emim TCB
Electrolyte 9 given in the molar ratio:
36 mmim I, 36 pmim I, 72 emim fluorotricyanoborate
Electrolyte 10 given in the molar ratio:
36 mmim I, 36 emim I, 72 emim fluorotricyanoborate
Electrolyte 11 given in the molar ratio:
36 mmim I, 36 amim I, 72 emim fluorotricyanoborate
Electrolyte 12 given in the molar ratio:
72 emim I, 72 emim fluorotricyanoborate
Electrolyte 13 given in the molar ratio:
36 mmim I, 36 mohmmim I, 72 emim fluorotricyanoborate
Electrolyte 14 given in the molar ratio:
36 mmim I, 36 mmpl I, 72 emim fluorotricyanoborate
Electrolyte 15 given in the molar ratio:
36 mmim I, 36 sm3 I, 72 emim fluorotricyanoborate
Electrolyte 16 given in the molar ratio:
36 mmim I, 8 pmim I, 12 amim I, 8 hmim I, 8 mmpl I, 72 emim fluorotricyanoborate The above cited compounds are commercially available or are synthesized according to known literature methods.

The dye sensitized solar cells are fabricated as disclosed in U.S. Pat. No. 5,728,487 or WO 2007/093961:

A double-layer, mesoporous $TiO_2$ electrode was prepared as disclosed in Wang P et al., J. Phys. Chem. B 2003, 107, 14336, in particular page 14337, in order to obtain a photoanode consisting of a double layer structure. To prepare a transparent nanoporous $TiO_2$ electrode, a screen printing paste containing terpineol solvent and nanoparticulate $TiO_2$ of anatase phase with 20 nm diameter was deposited on a transparent conductive substrate to 5 mm×5 mm squared shape by using a hand printer. The paste was dried for 10 minutes at 120 degrees Celsius. Another screen printing paste containing $TiO_2$ with 400 nm diameter was then deposited on top of the nanoporous layer to prepare an opaque layer. The double layer film was then sintered at 500 degrees Celsius for an hour with the result of an underlying transparent layer (7 microns thick) and a top opaque layer (4 microns thick). After sintering, the electrode was immersed in 40 mM aqueous solution of $TiCl_4$ (Merck) for 30 minutes at 70 degrees Celsius and then rinsed with pure water sufficiently. Thus $TiC_{1-4}$-treated electrode was dried at 500 degrees Celsius for 30 minutes just before dye sensitization. The electrode was dipped into a 0.3 mM Z907 dye solution of acetonitrile (Merck HPLC grade) and tert-butyl alcohol (Merck), v:v=1:1 for 60 hours at 19 degrees Celsius. The counter electrode was prepared with thermal pyrolysis method as disclosed in the reference above. A droplet of 5 mM solution of platinic acid (Merck) was casted at 8 μl/cm2 and dried on a conductive substrate. The dye sensitized solar cell was assembled by using 30 micron thick Bynel (DuPont, USA) hot-melt film to seal up by heating. The internal space was filled with each of the electrolyte formulations as described above to produce the corresponding devices.

The dye Z907 is an amphiphilic ruthenium sensitizer Ru(2,2'-bipyridine4,4'-dicarboxylic acid)(4,4'-dinonyl-2,2'-bipyridine)$(NCS)_2$ or $[Ru(H2dcbpy)(dnbpy)(NCS)_2]$.

The measurements of photocurrent-voltage curves are carried out under Air Mass 1.5 simulated sunlight (AM 1.5) with temperature control. A photomask of 4 mm×4 mm is placed on top of the devices fabricated according to example 3 to define the light projection area. The cell gap is in the range of 25 to 30 micron.

Energy conversion efficiency is generally the ratio between the useful output of an energy conversion machine and the input of light radiation, in energy terms, determined by using adjustable resistant load to optimize the electric power output.

Table 2 summarizes the results of the measurements of the above cited electrolyte formulations:

TABLE 2 summarizes the results of the measurements of the above cited electrolyte formulations:

| Electrolyte | $J_{SC}$ [mAcm$^{-2}$] | $V_{OC}$ [V] | FF | [%] |
|---|---|---|---|---|
| 1* | 8.71 | 0.70 | 0.71 | 3.65 |
| 2* | 8.37 | 0.67 | 0.68 | 3.85 |
| 3* | 9.30 | 0.67 | 0.68 | 3.88 |
| 4* | 8.11 | 0.66 | 0.66 | 3.52 |
| 5* | 8.14 | 0.68 | 0.69 | 3.68 |
| 6* | 8.44 | 0.67 | 0.63 | 3.57 |
| 7* | 8.52 | 0.67 | 0.72 | 3.66 |
| 8* | 8.61 | 0.66 | 0.67 | 3.81 |
| 9 | 8.51 | 0.68 | 0.70 | 4.06 |
| 10 | 7.77 | 0.69 | 0.69 | 3.71 |
| 11 | 7.72 | 0.69 | 0.71 | 3.74 |
| 12 | 8.81 | 0.66 | 0.69 | 4.06 |
| 13 | 8.40 | 0.66 | 0.67 | 3.68 |
| 14 | 8.17 | 0.69 | 0.70 | 3.90 |
| 15 | 8.36 | 0.66 | 0.67 | 3.42 |
| 16 | 8.42 | 0.66 | 0.63 | 3.51 |

*not according to the invention

Table 2 documents that electrolytes comprising fluorotricyanoborate as anion perform better or equal than electrolytes comprising TCB as anion if the same cation is used. The measurements of Electrolytes 2, 3, 7 and 8 and 10, 11, 15 and 16 were again repeated to confirm this statement.

EXAMPLE 3

Repetition of some electrolytes mentioned above in electrochemical devices as described in Example 2 and in electrochemical devices as described in Example 2 but using the dye Z907 (0.3 mM) together with 0.075 mM DINHOP Electrolyte 2 given in the molar ratio:
36 mmim I, 36 emim I, 72 emim TCB
Electrolyte 3 given in the molar ratio:
36 mmim I, 36 amim I, 72 emim TCB
36 mmiml, 36 mohmim I, 72 emim TCB
Electrolyte 7 given in the molar ratio:
36 mmim I, 36 sm3 I, 72 emim TCB
Electrolyte 8 given in the molar ratio:
36 mmim I, 8 pmim I, 12 amim I, 8 hmim I, 8 mmpl I, 72 emim TCB
Electrolyte 10 given in the molar ratio:
36 mmim I, 36 emim I, 72 emim fluorotricyanoborate
Electrolyte 11 given in the molar ratio:
36 mmim I, 36 amim I, 72 emim fluorotricyanoborate
Electrolyte 15 given in the molar ratio:
36 mmim I, 36 sm3 I, 72 emim fluorotricyanoborate
Electrolyte 16 given in the molar ratio:
36 mmim I, 8 pmim I, 12 amim I, 8 hmim I, 8 mmpl I, 72 emim fluorotricyanoborate The measurements are performed as described in Example 2.

TABLE 3 summarizes the results of the measurements of the above cited electrolyte formulations according to Example 2 with 0.3 mM Z907 as dye

| Electrolyte | $J_{SC}$ [mAcm$^{-2}$] | $V_{OC}$ [V] | FF | [%] |
|---|---|---|---|---|
| 2* | 8.37 | 0.71 | 0.73 | 4.09 |
| 3* | 8.35 | 0.70 | 0.69 | 4.06 |
| 7* | 7.63 | 0.69 | 0.74 | 3.86 |
| 8* | 9.29 | 0.68 | 0.67 | 4.06 |
| 10 | 8.58 | 0.73 | 0.74 | 4.14 |
| 11 | 8.85 | 0.69 | 0.71 | 4.09 |
| 15 | 7.89 | 0.68 | 0.72 | 3.86 |
| 16 | 9.57 | 0.68 | 0.63 | 4.10 |

*not according to the invention

TABLE 4 summarizes the results of the measurements of the above cited electrolyte formulations according to Example 2 with 0.3 mM Z907 as dye and 0.075 mM DINHOP

| Electrolyte | $J_{SC}$ [mAcm$^{-2}$] | $V_{OC}$ [V] | FF | [%] |
|---|---|---|---|---|
| 2* | 8.15 | 0.72 | 0.68 | 4.16 |
| 3* | 8.21 | 0.73 | 0.70 | 4.18 |
| 7* | 7.05 | 0.68 | 0.74 | 3.89 |
| 8* | 8.29 | 0.70 | 0.60 | 4.13 |
| 10 | 8.27 | 0.72 | 0.69 | 4.14 |
| 11 | 8.97 | 0.75 | 0.74 | 4.21 |
| 15 | 8.90 | 0.69 | 0.73 | 3.91 |
| 16 | 8.80 | 0.71 | 0.67 | 4.13 |

*not according to the invention

The invention claimed is:

1. An electrolyte formulation comprising at least one compound of formula (I)

$$Kt^+[BF(CN)_3]^- \qquad (I)$$

in which Kt$^+$ is an organic cation selection from the group of

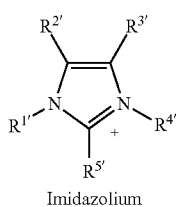  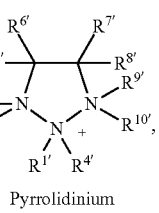

Imidazolium    Pyrrolidinium where the substituents
R$^{1'}$ to R$^{10'}$ each, independently of one another, denote
H with the assumption that R$^{1'}$ and R$^{4'}$ are not simultaneously H and are not perfluorinated at the same time,
straight-chain or branched alkyl having 1-20 C atoms, which optionally may be fluorinated or perfluorinated,
straight-chain or branched alkenyl having 2-20 C atoms and one or more double bonds, which optionally may be fluorinated or perfluorinated,
straight-chain or branched alkynyl having 2-20 C atoms and one or more triple bonds which optionally may be fluorinated or perfluorinated or
straight-chain or branched alkoxyalkyl having 2 to 8 C atoms and wherein the anion fluorotricyanoborate is in molar concentrations from 0.1 to 5.5 M.

2. The electrolyte formulation according to claim 1 in which Kt$^+$ of the compound of formula (I) is

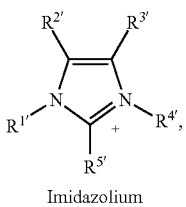

Imidazolium where the substituents R$^{2'}$ and R$^{3'}$ are H, R$^{5'}$ is H or straight-chain or branched alkyl having 1 to 4 C atoms and R$^{1'}$ and R$^{4'}$ are each independently of one another straight chain or branched alkyl having 1-20 C atoms or straight-chain or branched alkenyl having 3 C atoms.

3. The electrolyte formulation according to claim 1 in which Kt$^+$ of the compound of formula (I) is

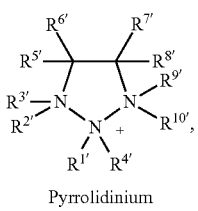

Pyrrolidinium where the substituents R$^{2'}$, R$^{3'}$, R$^{5'}$ to R$^{10'}$ are H and R$^{1'}$ and R$^{4'}$ are each independently of one another straight chain or branched alkyl having 1-20 C atoms.

4. An electrochemical and/or optoelectronic device comprising an electrolyte formulation comprising at least one compound of formula (I)

$$Kt^+[BF(CN)_3]^- \qquad (I)$$

in which Kt$^+$ is an organic cation selected from the group of

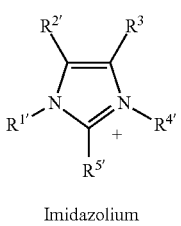  or  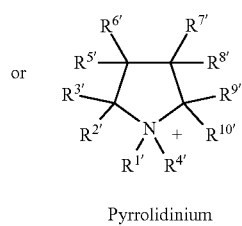

Imidazolium    Pyrrolidinium where the substituents
R$^{1'}$ to R$^{10'}$ each, independently of one another, denote
H with the assumption that R$^{1'}$ and R$^{4'}$ are not simultaneously H and are not perfluorinated at the same time,
straight-chain or branched alkyl having 1-20C atoms, which optionally may be fluorinated or perfluorinated,
straight-chain or branched alkenyl having 2-20 C atoms and one or more double bonds, which optionally may be fluorinated or perfluorinated,
straight-chain or branched alkynyl having 2-20 C atoms and one or more triple bonds which optionally may be fluorinated or perfluorinated or straight-chain or branched alkoxyalkyl having 2 to 8 C atoms, and wherein the electrochemical and/or optoelectronic device is a light emitting device, an electrochromic or photo-electrochromic device, an electrochemical sensor and/or biosensor.

5. The device according to claim 4 which is a dye or quantum dot sensitized solar cell.

6. The device according to claim 4 which is a dye sensitized solar cell.

7. The device according to claim 6, wherein said dye sensitized solar cell comprises a semiconductor, said electrolyte formulation and a counter electrode.

8. A method of operating an electrochemical and/or optoelectronic device which is a photovoltaic cell, a light emitting device, an electrochromic or photo-electrochromic device, an electrochemical sensor and/or biosensor, wherein said device contains an electrolyte formulation comprising at least one compound of formula (I)

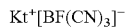
(I)

in which Kt$^+$ is an organic cation selected from the group of

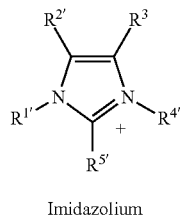 or 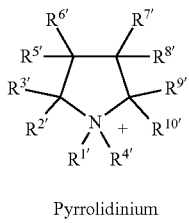

Imidazolium          Pyrrolidinium where the substituents

R$^{1'}$ to R$^{10'}$ each, independently of one another, denote

H with assumption that R$^{1'}$ and R$^{4'}$ are not simultaneously H and are not perfluorinated at the same time, straight-chain or branched alkyl having 1-20 C atoms, which optionally may be fluorinated or perfluorinated, straight-chain or branched alkynyl having 2-20 C atoms and one or more double bonds, which optionally may be fluorinated or perfluorinated, straight-chain or branched alkynyl having 2 to 20 C atoms and one or more triple bonds which optionally may be fluorinated or perfluorinated or straight-chain or branched alkoxyalkyl having 2 to 8 C atoms, and wherein said method comprises conducting electricity through said electrolyte formulation.

9. A method according to claim 8 in which the device is a dye sensitized solar cell.

10. The electrolyte formulation of claim 1 wherein the organic cation is selected from the group consisting of 1,1-dimethyl-pyrrolidinium, 1-methyl-1-ethylpyrrolidinium, 1-methyl-1-propyl-pyrrolidinium, 1-methyl-1-butylpyrrolidinium, 1-methyl-1-pentyl-pyrrolidinium, 1-methyl-1-hexylpyrrolidinium, 1-methyl-1-heptyl-pyrrolidinium, 1-methyl-1-octylpyrrolidinium, 1-methyl-1-nonyl-pyrrolidinium, 1-methyl-1-decylpyrrolidinium, 1,1-diethyl-pyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropyl-pyrrolidinium, 1-propyl-1-methylpyrrolidinium, 1-propyl-1-butyl-pyrrolidinium, 1-propyl-1-pentylpyrrolidinium, 1-propyl-1-hexyl-pyrrolidinium, 1-propyl-1-heptylpyrrolidinium, 1-propyl-1-octylpyrrolidinium, 1-propyl-1-nonylpyrrolidinium, 1-propyl-1-decyl-pyrrolidinium, 1,1-dibutylpyrrolidinium, 1-butyl-1-methyl-pyrrolidinium, 1-butyl-1-pentylpyrrolidinium, 1-butyl-1-hexyl-pyrrolidinium, 1-butyl-1-heptylpyrrolidinium, 1-butyl-1-octyl-pyrrolidinium, 1-butyl-1-nonylpyrrolidinium, 1-butyl-1-decyl-pyrrolidinium, 1,1-dipentylpyrrolidinium, 1-pentyl-1-hexyl-pyrrolidinium, 1-pentyl-1-heptylpyrrolidinium, 1-pentyl-1-octyl-pyrrolidinium, 1-pentyl-1-nonylpyrrolidinium, 1-pentyl-1-decyl-pyrrolidinium, 1,1-dihexylpyrrolidinium, 1-hexyl-1-heptyl-pyrrolidinium, 1-hexyl-1-octylpyrrolidinium, 1-hexyl-1-nonyl-pyrrolidinium, 1-hexyl-1-decylpyrrolidinium, 1,1-dihexyl-pyrrolidinium, 1-hexyl-1-heptylpyrrolidinium, 1-hexyl-1-octyl-pyrrolidinium, 1-hexyl-1-nonylpyrrolidinium, 1-hexyl-1-decyl-pyrrolidinium, 1,1-diheptylpyrrolidinium, 1-heptyl-1-octyl-pyrrolidinium, 1-heptyl-1-nonylpyrrolidinium, 1-heptyl-1-decyl-pyrrolidinium, 1,1-dioctylpyrrolidinium, 1-octyl-1-nonyl-pyrrolidinium, 1-octyl-1-decylpyrrolidinium, 1,1-dinonyl-pyrrolidinium, 1-nonyl-1-decylpyrrolidinium, 1,1-didecylpyrrolidinium, 1-butyl-1-methylpyrrolidinium, 1-propyl-1-methyl-pyrrolidinium, 1-(2-methoxyethyl)-1-methylpyrrolidinium, 1-(2-methoxyethyl)-1-ethylpyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-methyl-pyrrolidinium, 1-(2-methoxyethyl)-1-methylpyrrolidinium, 1-ethyl-3-methylimidazolium, 1-methyl-3-propylimidazolium, 1-methyl-2,3-dimethylimidazolium, 1-ethyl-2,3-dimethylimidazolium, 1-propyl-2,3-dimethylimidazolium, 1-butyl-2,3-dimethylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentyl-imidazolium, 1-butyl-3-propylimidazolium, 1,3-dimethyl-imidazolium, 1,3-diethylimidazolium, 1,3-dipropylimidazolium, 1,3-dibutylimidazolium, 1,3-dipentylimidazolium, 1,3-dihexylimidazolium, 1,3-diheptyl-imidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonyl-imidazolium, 1-decyl-3-methylimidazolium, 1-ethyl-3-hexyl-imidazolium, 1-ethyl-3-heptylimidazolium, 1-ethyl-3-octyl-imidazolium, 1-ethyl-3-nonylimidazolium, 1-decyl-3-ethyl-imidazolium, 1-ethyl-3-methylimidazolium, 1-butyl-3-methyl-imidazolium, 1-methyl-3-propylimidazolium, 1-(2-methoxyethyl)-3-methylimidazolium, 1-(2-methoxyethyl)-3-ethylimidazolium, 1-(2-methoxyethyl)-3-propylimidazolium, 1-(2-methoxyethyl)-3-butyl-imidazolium, 1-(2-ethoxyethyl)-3-methylimidazolium, 1-ethoxymethyl-3-methylimidazolium, 1-allyl-3-methyl-imidazolium, and 1-allyl-2,3-dimethylimidazolium.

11. The electrochemical and/or optoelectronic device of claim 4 wherein the organic cation is selected from the group consisting of 1,1-dimethylpyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethyl-pyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropyl-pyrrolidinium, 1-propyl-1-methylpyrrolidinium, 1-propyl-1-butyl-pyrrolidinium, 1-propyl-1-pentylpyrrolidinium, 1-propyl-1-hexyl-pyrrolidinium, 1-propyl-1-heptylpyrrolidinium, 1-propyl-1-octyl-pyrrolidinium, 1-propyl-1-nonylpyrrolidinium, 1-propyl-1-decylpyrrolidinium, 1,1-dibutylpyrrolidinium, 1-butyl-1-methyl-pyrrolidinium, 1-butyl-1-pentylpyrrolidinium, 1-butyl-1-hexyl-pyrrolidinium, 1-butyl-1-heptylpyrrolidinium, 1-butyl-1-octyl-pyrrolidinium, 1-butyl-1-nonylpyrrolidinium, 1-butyl-1-decyl-pyrrolidinium, 1,1-dipentylpyrrolidinium, 1-pentyl-1-hexyl-pyrrolidinium, 1-pentyl-1-heptylpyrrolidinium, 1-pentyl-1-octyl-pyrrolidinium, 1-pentyl-1-nonylpyrrolidinium, 1-pentyl-1-decyl-pyrrolidinium, 1,1-dihexylpyrrolidinium, 1-hexyl-1-heptyl-pyrrolidinium, 1-hexyl-1-octylpyrroli-dinium, 1-hexyl-1-nonyl-pyrrolidinium, 1-hexyl-1-decylpyr-rolidinium, 1,1-dihexyl-pyrrolidinium, 1-hexyl-1-heptylpyr-rolidinium, 1-hexyl-1-octyl-pyrrolidinium, 1-hexyl-1-nonylpyrrolidinium, 1-hexyl-1-decyl-pyrrolidinium, 1,1-diheptylpyrrolidinium, 1-heptyl-1-octyl-pyrrolidinium, 1-heptyl-1-nonylpyrrolidinium, 1-heptyl-1-decyl-pyrroli-dinium, 1,1-dioctylpyrrolidinium, 1-octyl-1-nonyl-pyrroli-dinium, 1-octyl-1-decylpyrrolidinium, 1,1-dinonyl-pyrroli-dinium, 1-nonyl-1-decylpyrrolidinium, 1,1-didecylpyrrolidinium, 1-butyl-1-methylpyrrolidinium 1-propyl-1-methyl-pyrrolidinium, 1-(2-methoxyethyl)-1-methylpyrrolidinium, 1-(2-methoxyethyl)-1-ethylpyrroli-dinium, 1-(2-methoxyethyl)-1-propyl-pyrrolidinium, 1-(2-methoxyethyl)-1-butylpyrrolidinium, 1-(2-ethoxyethyl)-1-methylpyrrolidinium, 1-ethoxymethyl-1-methyl-pyrrolidinium, 1-(2-methoxyethyl)-1-methylpyrrolidinium 1-ethyl-3-methylimidazolium, 1-methyl-3-propylimidazo-lium, 1-methyl-2,3-dimethylimidazolium, 1-ethyl-2,3-dim-ethylimidazolium, 1-propyl-2,3-dimethylimidazolium, 1-bu-tyl-2,3-dimethylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentyl-imidazolium, 1-butyl-3-propylimidazo-lium, 1,3-dimethylimidazolium, 1,3-diethylimidazolium, 1,3-dipropylimidazolium, 1,3-dibutylimidazolium, 1,3-di-pentylimidazolium, 1,3-dihexylimidazolium, 1,3-diheptyl-imidazolium, 1,3-dioctylimidazolium, 1,3-dinonylimidazo-lium, 1,3-didecylimidazolium, 1-hexyl-3-methylimidazolium, 1-heptyl-3-methylimidazolium, 1-methyl-3-octylimidazolium, 1-methyl-3-nonyl-imidazo-lium, 1-decyl-3-methylimidazolium, 1-ethyl-3-hexyl-imida-zolium, 1-ethyl-3-heptylimidazolium, 1-ethyl-3-octyl-imi-dazolium, 1-ethyl-3-nonylimidazolium, 1-decyl-3-ethyl-imidazolium, 1-ethyl-3-methylimidazolium, 1-butyl-3-methyl-imidazolium, 1-methyl-3-propylimidazolium 1-(2-methoxyethyl)-3-methylimidazolium, 1-(2-methoxyethyl)-3-ethylimidazolium, 1-(2-methoxyethyl)-3-propylimidazolium, 1-(2-methoxyethyl)-3-butyl-imidazolium, 1-(2-ethoxyethyl)-3-methylimidazolium, 1-ethoxymethyl-3-methylimidazolium, 1-allyl-3-methyl-imidazolium, and 1-allyl-2,3-dimethylimidazolium.

12. The electrolyte formulation of claim 1 wherein the electrolyte formulation additionally comprises from 0.0005 to 7 mol/dm³ of iodine.

13. The electrochemical and/or optoelectronic device of claim 4 wherein the electrolytic formulation additionally comprises from 0.0005 to 7 mol/dm³ of iodine.

14. The electrolyte formulation of claim 1 wherein the electrolyte formulation additionally comprises from 0.01 to 5 mol/dm³ of iodine.

15. The electrochemical and/or optoelectronic device of claim 4 wherein the electrolytic formulation additionally comprises from 0.01 to 5 mol/dm³ of iodine.

16. The electrolyte formulation of claim 1 wherein the electrolyte formulation additionally comprises from 0.05 to 1 mol/dm³ of iodine.

17. The electrochemical and/or optoelectronic device of claim 4 wherein the electrolytic formulation additionally comprises from 0.05 to 1 mol/dm³ of iodine.

18. The electrolyte formulation of claim 1 additionally comprising an organic solvent wherein the electrolyte formulation comprises less than 50 vol. % of the organic solvent.

19. The electrochemical and/or optoelectronic device of claim 4 additionally comprising an organic solvent wherein the electrolyte formulation comprises less than 50 vol. % of the organic solvent.

20. The electrolyte formulation of claim 18 wherein the organic solvent is selected from the group consisting of pro-pylene carbonate, ethylene carbonate, butylene carbonate, gamma-butyrolactone, gamma-valerolactone, glutaronitrile, adiponitrile, N-methyloxazolidinone, N-methylpyrrolidi-none, N,N'-dimethylimidazolidinone, N,N-dimethylaceta-mide, 1,3-dimethyl-2-imidazolidinone or 1,3-dimethyl-3,4,5,6-tetrahydro-2(1H)-pyrimidinone, tetraglyme, sulfolane, 2-ethanesulfonyl-propane, 1-ethanesulfonyl-2-methyl-pro-pane or 2-(propane-2-sulfonyl)-butane, 3-methylsulfolane, dimethylsulfoxide, trimethylphosphate, methoxy-substituted nitriles, acetonitrile, benzonitrile and valeronitrile.

21. The electrochemical and/or optoelectronic device of claim 19 wherein the organic solvent is selected from the group consisting of propylene carbonate, ethylene carbonate, butylene carbonate, gamma-butyrolactone, gamma-valero-lactone, glutaronitrile, adiponitrile, N-methyloxazolidinone, N-methylpyrrolidinone, N,N'-dimethylimidazolidinone, N,N-dimethylacetamide, 1,3-dimethyl-2-imidazolidinone or 1,3-dimethyl-3,4,5,6-tetrahydro-2(1H)-pyrimidinone, tetra-glyme, sulfolane, 2-ethanesulfonyl-propane, 1-ethanesulfo-nyl-2-methyl-propane or 2-(propane-2-sulfonyl)-butane, 3-methylsulfolane, dimethylsulfoxide, trimethylphosphate, methoxy-substituted nitriles, acetonitrile, benzonitrile and valeronitrile.

22. The electrolyte formulation of claim 1 which addition-ally comprises 1-ethyl-3-methylimidazolium iodide, 1-pro-pyl-3-methylimidazolium iodide, 1-butyl-3-methyl-imida-zolium iodide, 1-hexyl-3-methylimidazolium iodide, 1,3-dimethyl-imidazolium iodide, 1-allyl-3-methylimidazolium iodide, N-butyl-N-methyl-pyrrolidinium iodide or N,N-dim-ethyl-pyrrolidinium iodide.

23. The electrochemical and/or optoelectronic device of claim 4 which additionally comprises 1-ethyl-3-methylimi-dazolium iodide, 1-propyl-3-methylimidazolium iodide, 1-butyl-3-methyl-imidazolium iodide, 1-hexyl-3-methylimi-dazolium iodide, 1,3-dimethyl-imidazolium iodide, 1-allyl-3-methylimidazolium iodide, N-butyl-N-methyl-pyrroli-dinium iodide or N,N-dimethyl-pyrrolidinium iodide.

24. The electrolyte formulation of claim 4 wherein the electrolyte formulation additionally comprises at least one iodide in which the organic cation is selected from the group of

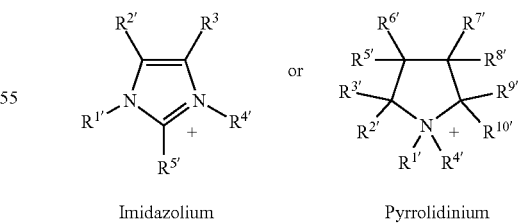

Imidazolium                Pyrrolidinium where the substitute is $R^{1'}$ to $R^{10'}$ independently of one another, denote H with the assumption that $R^{1'}$ and $R^{4'}$ are not simulta-neously H and are not perfluorinated at the same time, straight-chain or branched alkyl having 1-20 C atoms, which optionally may be fluorinated or perfluorinated, straight-chain or branched alkenyl having 2-20 C atoms and one or more double bonds, which optionally may be fluorinated or perfluorinated, straight-chain or branched alkynyl having 2-20 C atoms and one or more triple bonds which optionally may be fluorinated or perfluorinated or straight-chain or branched alkoxyalkyl having 2 to 8 C atoms.

25. An electrochemical and/or optoelectronic device of claim 4 wherein the electrolyte formulation additionally comprises at least one iodide in which the organic cation is selected from the group of

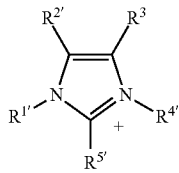

Imidazolium

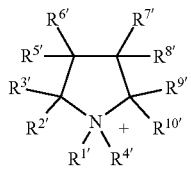

Pyrrolidinium where the substitute is $R^{1'}$ to $R^{10'}$ independently of one another, denote H with the assumption that $R^{1'}$ and $R^{4'}$ are not simultaneously H and are not perfluorinated at the same time, straight-chain or branched alkyl having 1-20 C atoms, which optionally may be fluorinated or perfluorinated, straight-chain or branched alkenyl having 2-20 C atoms and one or more double bonds, which optionally may be fluorinated or perfluorinated, straight-chain or branched alkynyl having 2-20 C atoms and one or more triple bonds which optionally may be fluorinated or perfluorinated or straight-chain or branched alkoxyalkyl having 2 to 8 C atoms.

26. The electrochemical and/or optoelectronic device according to claim 4 in which $Kt^+$ of the compound of formula (I) is

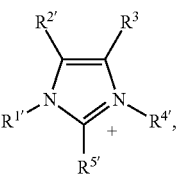

Imidazolium where the substituents $R^{2'}$ and $R^{3'}$ are H, $R^{5'}$ is H or straight-chain or branched alkyl having 1 to 4 C atoms and $R^{1'}$ and $R^{4'}$ are each independently of one another straight chain or branched alkyl having 1-20 C atoms or straight-chain or branched alkenyl having 3 C atoms.

27. The electrochemical and/or optoelectronic device according to claim 4 in which $Kt^+$ of the compound of formula (I) is

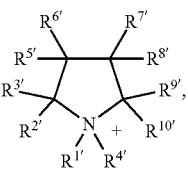

Pyrrolidinium where the substituents $R^{2'}$, $R^{3'}$, $R^{5'}$ to $R^{10'}$ are H and $R^{1'}$ and $R^{4'}$ are each independently of one another straight chain or branched alkyl having 1-20 C atoms.

* * * * *